(12) United States Patent
Nageri et al.

(10) Patent No.: US 10,342,983 B2
(45) Date of Patent: Jul. 9, 2019

(54) SYSTEMS AND METHODS FOR MAKING AND USING CONNECTOR CONTACT ARRAYS FOR ELECTRICAL STIMULATION SYSTEMS

(71) Applicant: Boston Scientific Neuromodulation Corporation, Valencia, CA (US)

(72) Inventors: Ranjan Krishna Mukhari Nageri, Valencia, CA (US); Geoffrey Abellana Villarta, Valencia, CA (US); Anne M. Pianca, Santa Monica, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 236 days.

(21) Appl. No.: 15/403,029

(22) Filed: Jan. 10, 2017

(65) Prior Publication Data
US 2017/0203104 A1    Jul. 20, 2017

Related U.S. Application Data

(60) Provisional application No. 62/278,667, filed on Jan. 14, 2016.

(51) Int. Cl.
*A61N 1/375* (2006.01)
*A61N 1/05* (2006.01)
(Continued)

(52) U.S. Cl.
CPC .......... *A61N 1/3752* (2013.01); *A61B 5/0478* (2013.01); *A61B 5/6868* (2013.01);
(Continued)

(58) Field of Classification Search
CPC .............. A61N 1/3752; Y10S 439/909; H01R 2201/12
See application file for complete search history.

(56) References Cited

U.S. PATENT DOCUMENTS 3,222,471 A    12/1965 Steinkamp
3,601,747 A     8/1971 Prall et al.
(Continued)

FOREIGN PATENT DOCUMENTS

EP    0580928 A1    2/1994
EP    0650694 B1    7/1998
(Continued)

*Primary Examiner* — George R Evanisko
(74) *Attorney, Agent, or Firm* — Lowe Graham Jones PLLC; Bruce E. Black

(57) ABSTRACT

A connector for an implantable electrical medical device can include a connector housing having a first portion and a second portion that can partially separate to receive a lead or lead extension into a connector lumen of the connector housing. The connector also includes at least one connector magnetic element coupled to each of the first and second portions of the connector housing to couple to at least one corresponding magnetic element in the lead or lead extension to align the lead or lead extension within the connector lumen of the connector housing. An electrical stimulation lead can include at least one lead magnetic element disposed along the proximal end of the lead body to couple to at least one corresponding magnetic element in a connector to align the lead within a connector lumen of the connector.

19 Claims, 11 Drawing Sheets

(51) Int. Cl.
*A61B 5/00* (2006.01)
*A61B 5/0478* (2006.01)

(52) U.S. Cl.
CPC ........ *A61N 1/0551* (2013.01); *A61B 2505/05* (2013.01); *A61B 2505/09* (2013.01); *A61B 2562/043* (2013.01); *A61B 2562/046* (2013.01); *A61B 2562/227* (2013.01)

(56) References Cited

U.S. PATENT DOCUMENTS

| | | |
|---|---|---|
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Karnaji et al. |
| 6,181,989 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |

(56) References Cited

U.S. PATENT DOCUMENTS

| | | |
|---|---|---|
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Erase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brace |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |

(56) References Cited

U.S. PATENT DOCUMENTS

| | | |
|---|---|---|
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0009192 A1* | 1/2008 | Kast .................. A61N 1/3752 439/607.41 |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Bays et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0042169 A1* | 2/2010 | Barker ................ A61N 1/3752 607/2 |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0114210 A1* | 5/2010 | Donofrio ............. A61N 1/3752 607/5 |
| 2010/0268296 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0100729 A1* | 4/2012 | Edidin ............... H01R 13/6205 439/38 |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffitt et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0250466 A1* | 9/2016 | Boggs, II ........... A61N 1/36021 607/46 |
| 2016/0296745 A1 | 10/2016 | Govea et al. |
| 2016/0375238 A1 | 12/2016 | Leven et al. |
| 2017/0056652 A1* | 3/2017 | Gittard ................ A61N 1/0507 |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |
| 2018/0243570 A1 | 8/2018 | Malinowski et al. |
| 2018/0289968 A1 | 10/2018 | Lopez |

(56) References Cited

U.S. PATENT DOCUMENTS

| | | |
|---|---|---|
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

\* cited by examiner

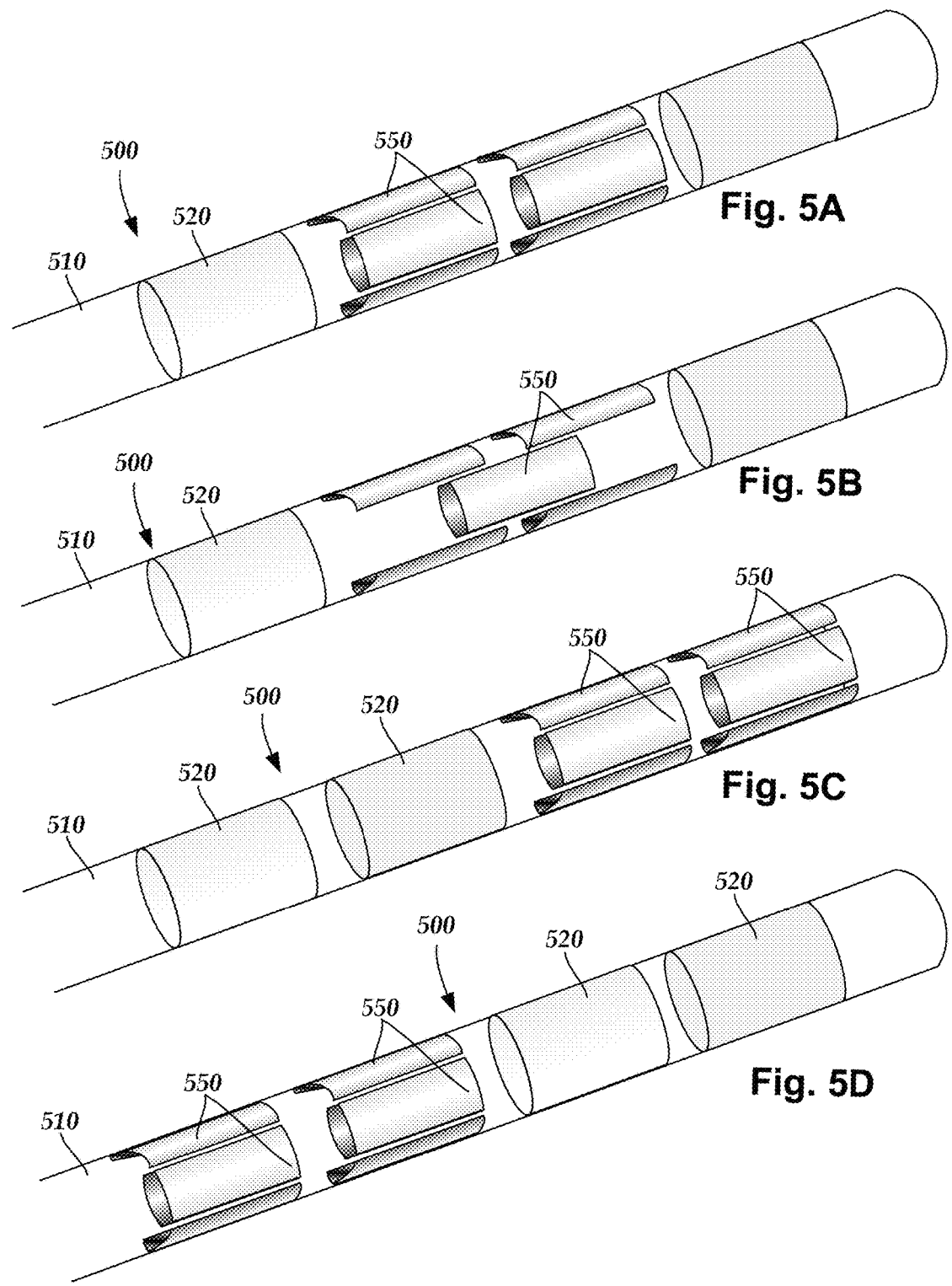

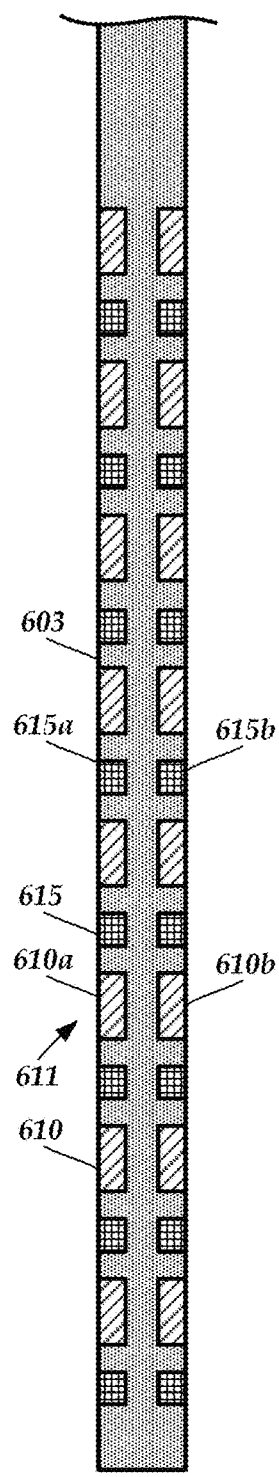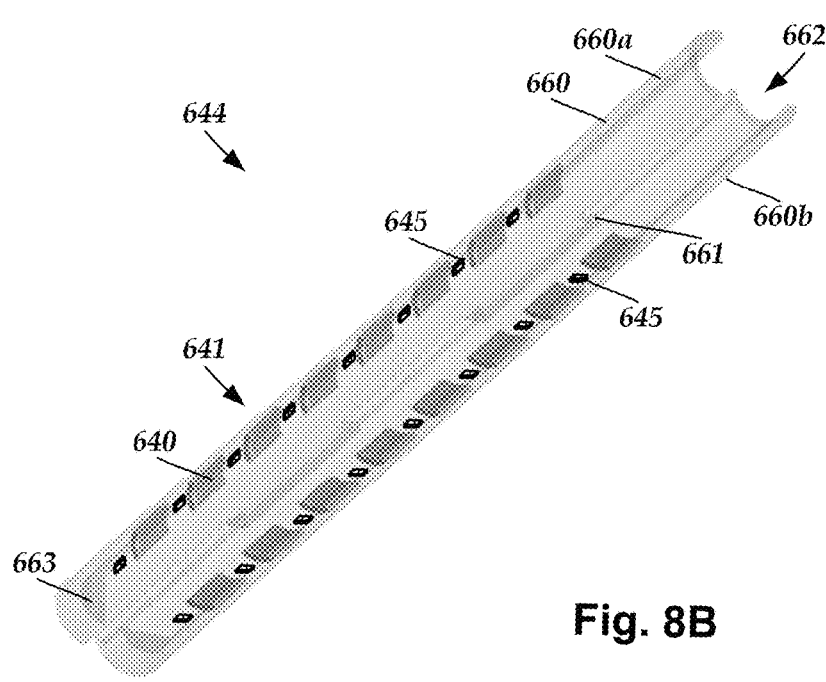
Fig. 8A
Fig. 8B

SYSTEMS AND METHODS FOR MAKING AND USING CONNECTOR CONTACT ARRAYS FOR ELECTRICAL STIMULATION SYSTEMS

CROSS-REFERENCE TO RELATED APPLICATIONS

This application claims the benefit under 35 U.S.C. § 119(e) of U.S. Provisional Patent Application Ser. No. 62/278,667, filed Jan. 14, 2016, which is incorporated herein by reference.

FIELD

The present invention is directed to the area of implantable electrical stimulation systems and methods of making and using the systems. The present invention is also directed to implantable electrical stimulation systems having connector contact arrays for receiving split proximal contact arrays, as well as methods of making and using the elongated devices, contact arrays, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a connector for an implantable electrical stimulation device. The connector includes an elongated connector housing having a first end and an opposing second end, the connector housing including a first portion, a second portion, at least one coupling element attaching the first portion to the second portion, and a connector lumen defined by the first and second portions, where the first and second portions are configured and arranged to partially separate to receive a lead or lead extension into the connector lumen of the connector housing. The connector also includes connector contacts disposed on the connector housing adjacent the connector lumen, where a first set of the connector contacts is disposed on the first portion of the connector housing and a second set of the connector contacts is disposed on the second portion of the connector housing; and at least one connector magnetic element coupled to each of the first and second portions of the connector housing to couple to at least one corresponding magnetic element in the lead or lead extension to align the lead or lead extension within the connector lumen of the connector housing.

In at least some embodiments, at least one of the connector contacts is the at least one connector magnetic element. In at least some embodiments, the at least one connector magnetic element is part of the connector housing. In at least some embodiments, at least one of the at least one connector magnetic element is disposed between two of the connector contacts.

In at least some embodiments, the first portion and the second portion of the connector housing have a tongue and groove arrangement along edges of the first and second portions to fasten the first and second portions in a closed position. In at least some embodiments, the first portion and the second portion of the connector housing each have at least one magnet disposed edges of the first and second portions to fasten the first and second portions in a closed position. In at least some embodiments, the at least one coupling element of the connector housing is at least one hinge.

Another embodiment is a lead extension that includes any of the connectors described above; a lead extension body extending from the connector; terminal disposed along a portion of the lead extension body opposite the connector; and conductors extending along the lead extension body and the connector and electrically coupling the connector contacts to the terminals.

Yet another embodiment is a control module that includes a header having one of the connector described above; a housing coupled to a header; and an electronic subassembly disposed within the housing, where the electronic subassembly is electrically coupled to the connector contacts of the connector.

A further embodiment is an electrical stimulation lead including an elongate lead body having a proximal end and a distal end opposite the proximal end; electrodes disposed along the distal end of the lead body; terminals disposed along the proximal end of the lead body; conductors extending within the lead body and electrically coupling the electrodes to the terminals; and at least one lead magnetic element disposed along the proximal end of the lead body to couple to at least one corresponding magnetic element in a connector to align the lead within a connector lumen of the connector.

In at least some embodiments, at least one of the terminals is the at least one lead magnetic element. In at least some embodiments, the at least one lead magnetic element is part of the lead body. In at least some embodiments, at least one of the at least one lead magnetic element is disposed between two of the terminals.

Another embodiment is a system for electrical stimulation that includes any one of the connectors described above and any one of the electrical stimulation leads described above. In at least some embodiments, at least one of the connector contacts is the at least one connector magnetic element and at least one of the terminals is the at least one lead magnetic element. In at least some embodiments, the at least one connector magnetic element is part of the connector housing and the at least one lead magnetic element is part of the lead body. In at least some embodiments, at least one of the at least one connector magnetic element is disposed between two of the connector contacts and at least one of the at least one lead magnetic element is disposed between two of the terminals. In at least some embodiments, the at least one coupling element of the connector housing is at least one hinge.

In at least some embodiments, the system further includes a lead extension having the connector; a lead extension body extending from the connector; terminals disposed along a portion of the lead extension body opposite the connector; and conductors extending along the lead extension body and the connector and electrically coupling the connector contacts to the terminals.

In at least some embodiments, the system further includes a control module having a header including the connector; a housing coupled to a header; and an electronic subassembly disposed within the housing, where the electronic subassembly is electrically coupled to the connector contacts of the connector.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic perspective view of one embodiment of a distal end of a lead containing segmented electrodes, according to the invention;

FIG. 5B is a schematic perspective view of a second embodiment of a distal end of a lead containing segmented electrodes, according to the invention;

FIG. 5C is a schematic perspective view of a third embodiment of a distal end of a lead containing segmented electrodes, according to the invention;

FIG. 5D is a schematic perspective view of a fourth embodiment of a distal end of a lead containing segmented electrodes, according to the invention;

FIG. 8A is a schematic side view of a fourth embodiment of a proximal end of a lead containing segmented terminals, according to the invention;

FIG. 8B is schematic perspective view of one embodiment of a connector for receiving the lead of FIG. 8A, according to the invention.

DETAILED DESCRIPTION

The present invention is directed to the area of implantable electrical stimulation systems and methods of making and using the systems. The present invention is also directed to implantable electrical stimulation systems having connector contact arrays for receiving split proximal contact arrays, as well as methods of making and using the elongated devices, contact arrays, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entirety.

Figure 1:
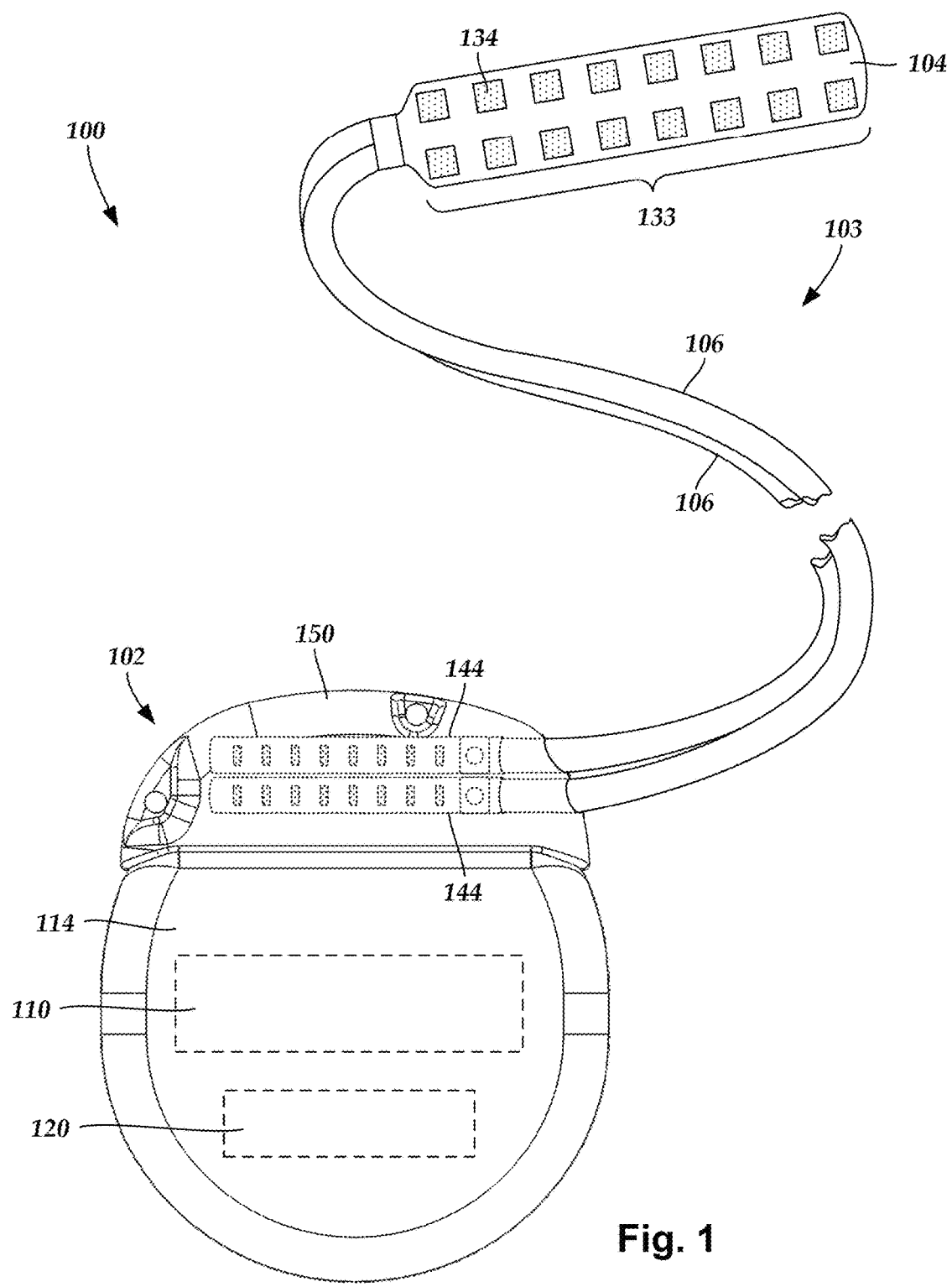
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals (e.g., 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102. The connectors 144 are electrically coupled to the electronic subassembly 110 through a feedthrough arrangement between the header 150 and the sealed housing 114.

Figure 2:
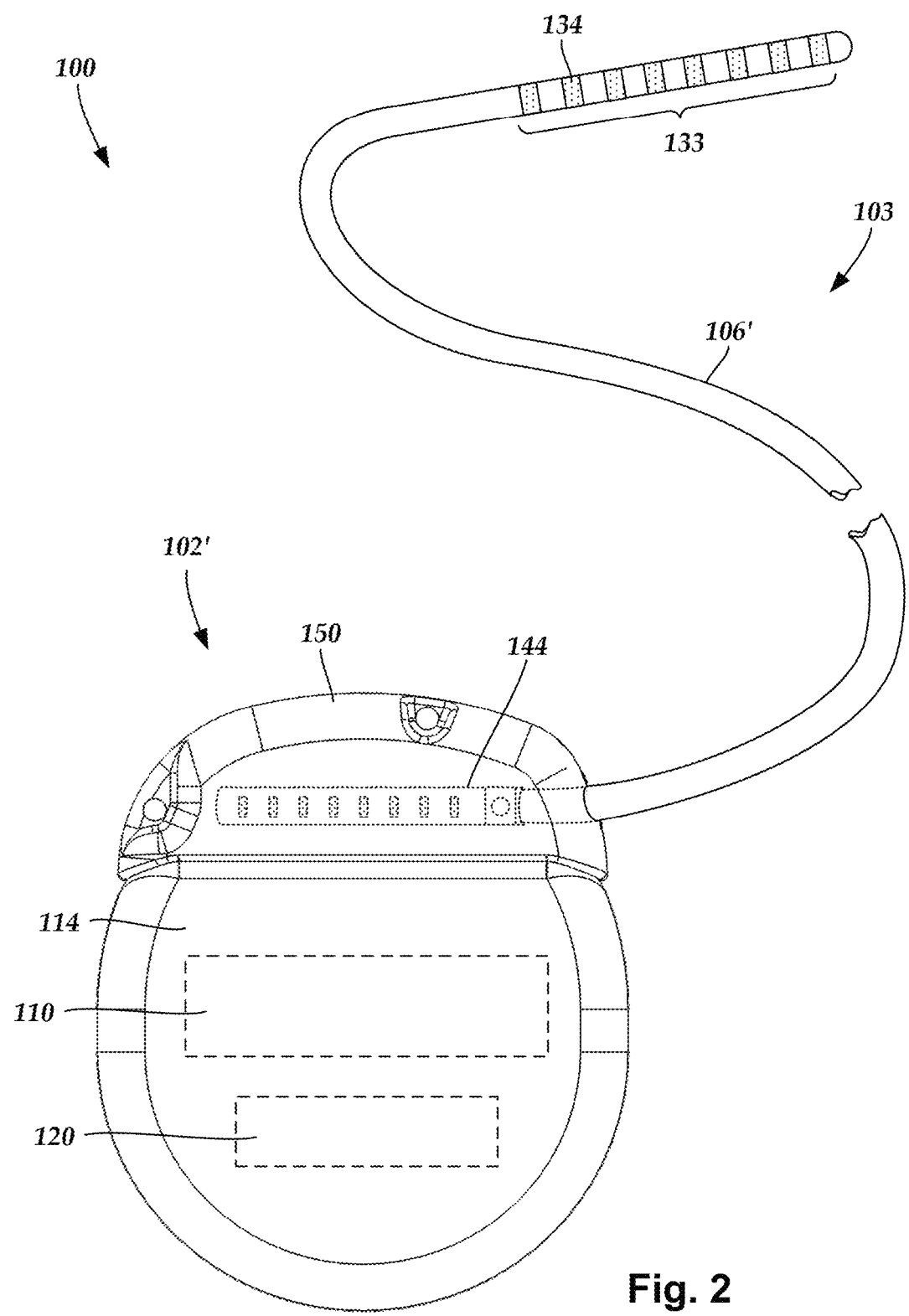
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3A:
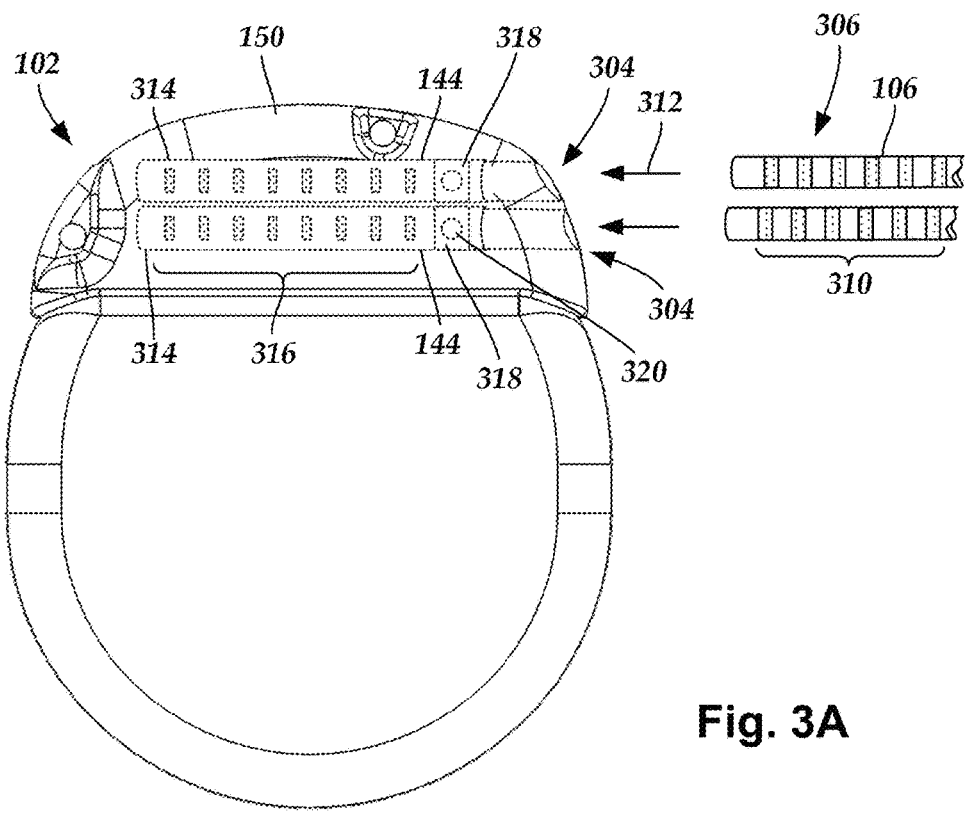
FIG. 3A is a schematic view of one embodiment of a plurality of connectors disposed in the control module of FIG. 1, the connectors configured and arranged to receive the proximal portions of the lead bodies of FIG. 1, according to the invention.
Figure 3B:
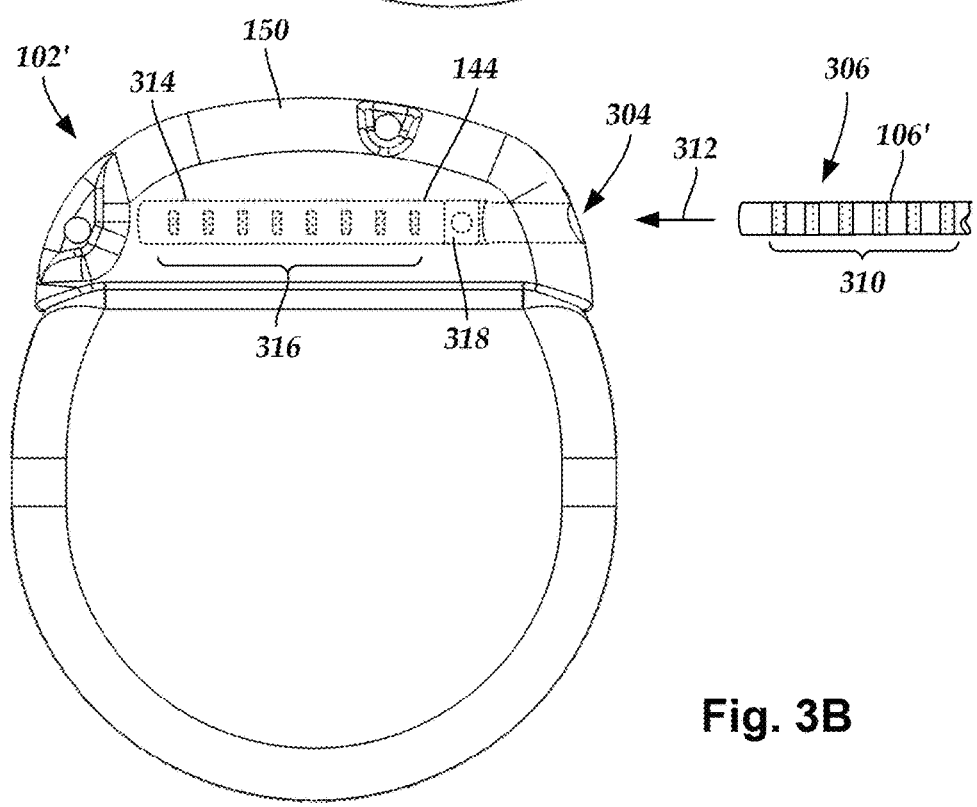
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 6,224,450, which are incorporated by reference in their entirety.

Figure 3C:
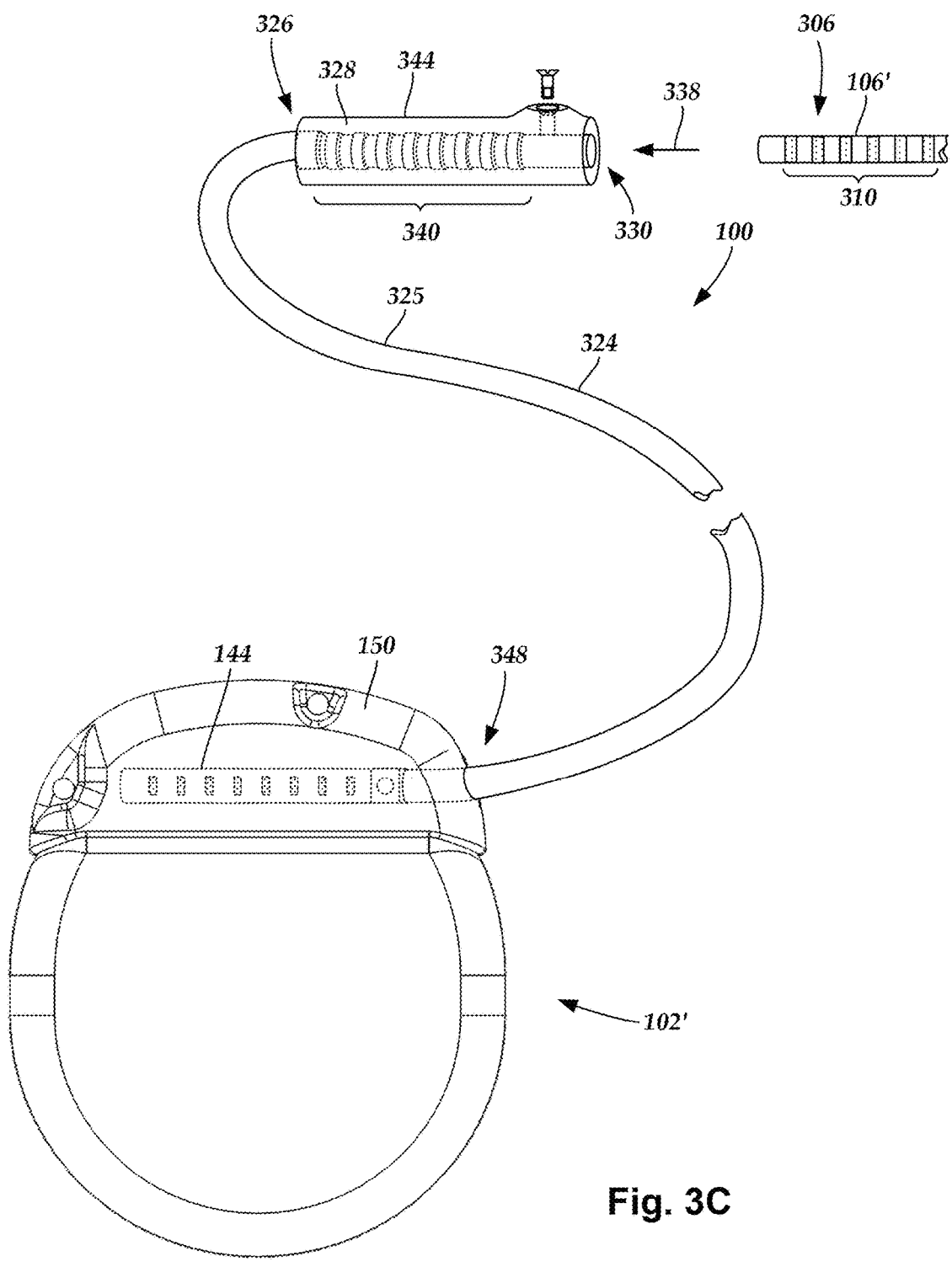
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324 and is coupled to a lead extension body 325. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 322 also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 324. For example, each of the lead bodies 106 shown in FIGS. 1 and 3A can, alternatively, be coupled to a different lead extension 324 which, in turn, are each coupled to different ports of a two-port control module, such as the control module 102 of FIGS. 1 and 3A.

Figure 4:
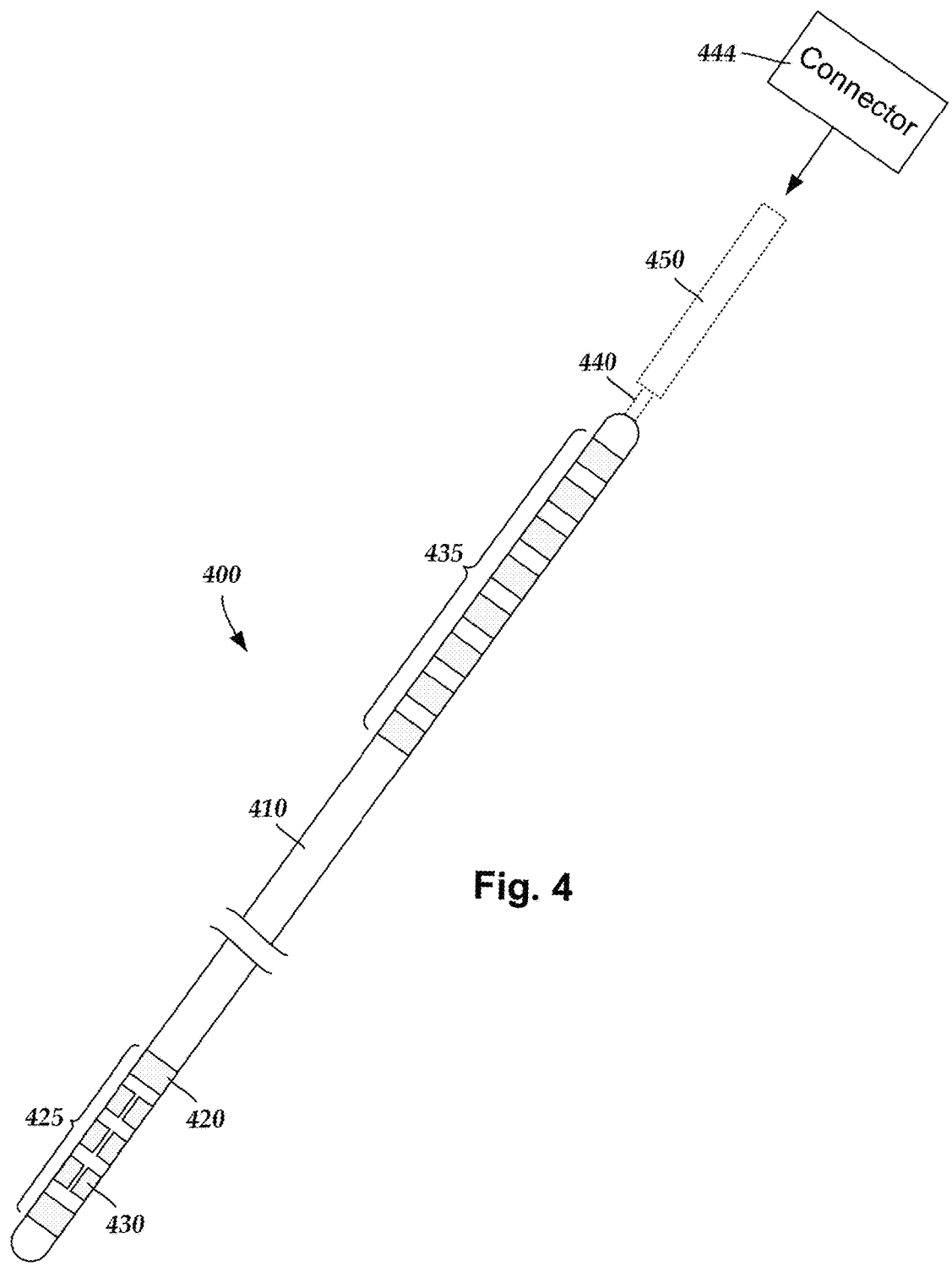
FIG. 4 is a schematic side view of yet another embodiment of an implantable medical device for brain stimulation, according to the invention.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a perimeter of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

In FIG. 4, the electrodes 425 are shown as including both ring electrodes, such as ring electrode 420, and segmented electrodes, such as segmented electrodes 430. In some embodiments, the electrodes 425 are all segmented. In other embodiments, the electrodes 425 are all ring-shaped. In FIG. 4, each of the terminals 435 is shown as being ring-shaped. The segmented electrodes of FIG. 4 are shown in sets of two, where the two segmented electrodes of a particular set are electrically isolated from one another and are circumferentially offset along the lead 410. Any suitable number of segmented electrodes can be formed into a set including, for example, two, three, four, or more segmented electrodes.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue. Examples of leads with segmented electrodes include U.S. Pat. Nos. 6,295,944; and 6,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference in their entirety.

Figure 5E:
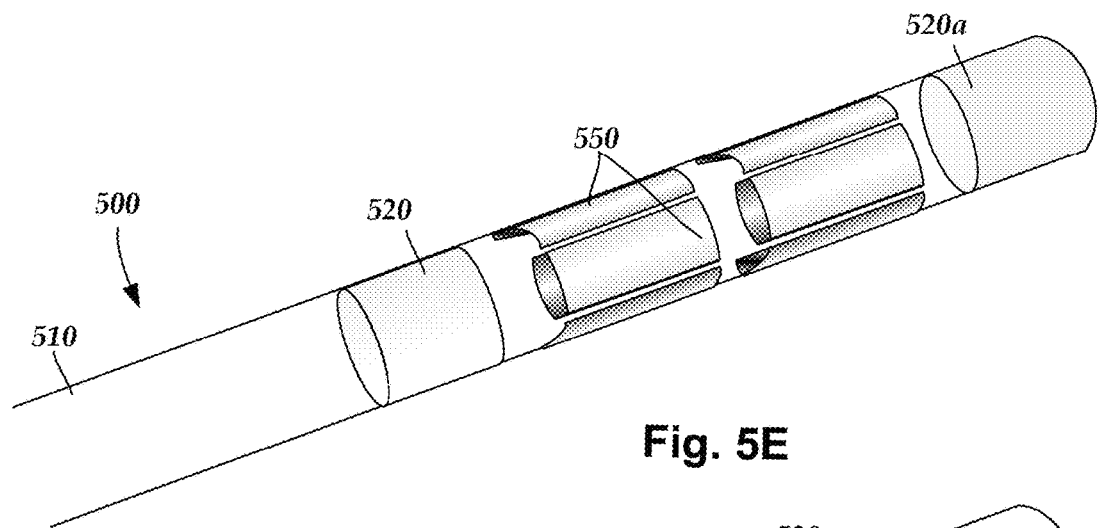
FIG. 5E is a schematic perspective view of a fifth embodiment of a distal end of a lead containing segmented electrodes, according to the invention.
Figure 5F:
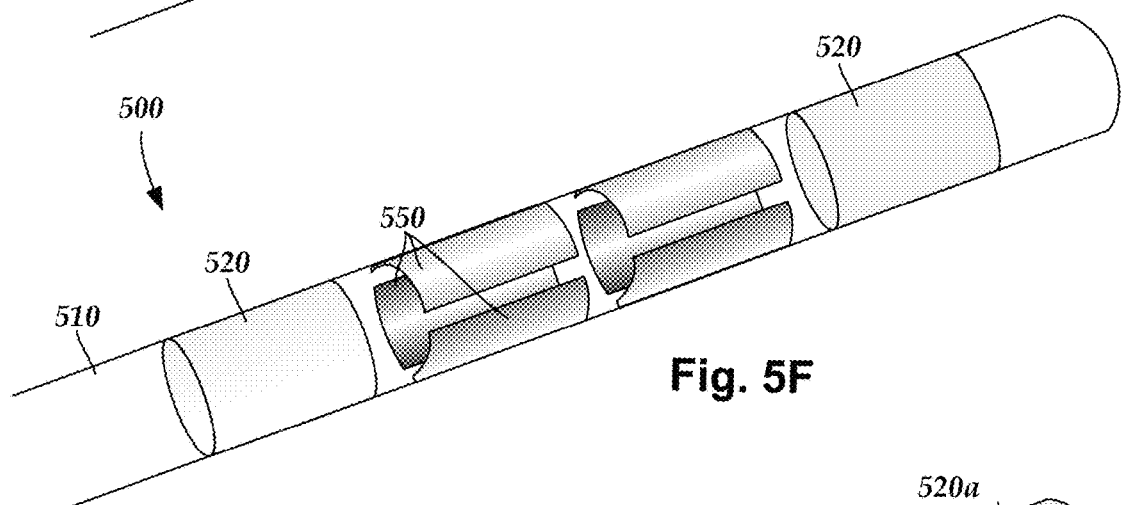
FIG. 5F is a schematic perspective view of a sixth embodiment of a distal end of a lead containing segmented electrodes, according to the invention.

FIGS. 5A-5H illustrate leads 500 with segmented electrodes 550, optional ring electrodes 520 or tip electrodes 520a, and a lead body 510. The sets of segmented electrodes 550 each include either two (FIG. 5B), three (FIGS. 5E-5H), or four (FIGS. 5A, 5C, and 5D) or any other number of segmented electrodes including, for example, three, five, six, or more. The sets of segmented electrodes 550 can be aligned with each other (FIGS. 5A-5G) or staggered (FIG. 5H).

When the lead 500 includes both ring electrodes 520 and segmented electrodes 550, the ring electrodes 520 and the segmented electrodes 550 may be arranged in any suitable configuration. For example, when the lead 500 includes two ring electrodes 520 and two sets of segmented electrodes 550, the ring electrodes 520 can flank the two sets of segmented electrodes 550 (see e.g., FIGS. 1, 5A, and 5E-5H). Alternately, the two sets of ring electrodes 520 can be disposed proximal to the two sets of segmented electrodes 550 (see e.g., FIG. 5C), or the two sets of ring electrodes 520 can be disposed distal to the two sets of segmented electrodes 550 (see e.g., FIG. 5D). One of the ring electrodes can be a tip electrode (see, tip electrode 520a of FIGS. 5E and 5G). It will be understood that other configurations are possible as well (e.g., alternating ring and segmented electrodes, or the like).

By varying the location of the segmented electrodes 550, different coverage of the target neurons may be selected. For example, the electrode arrangement of FIG. 5C may be useful if the physician anticipates that the neural target will be closer to a distal tip of the lead body 510, while the electrode arrangement of FIG. 5D may be useful if the physician anticipates that the neural target will be closer to a proximal end of the lead body 510.

Figure 5G:
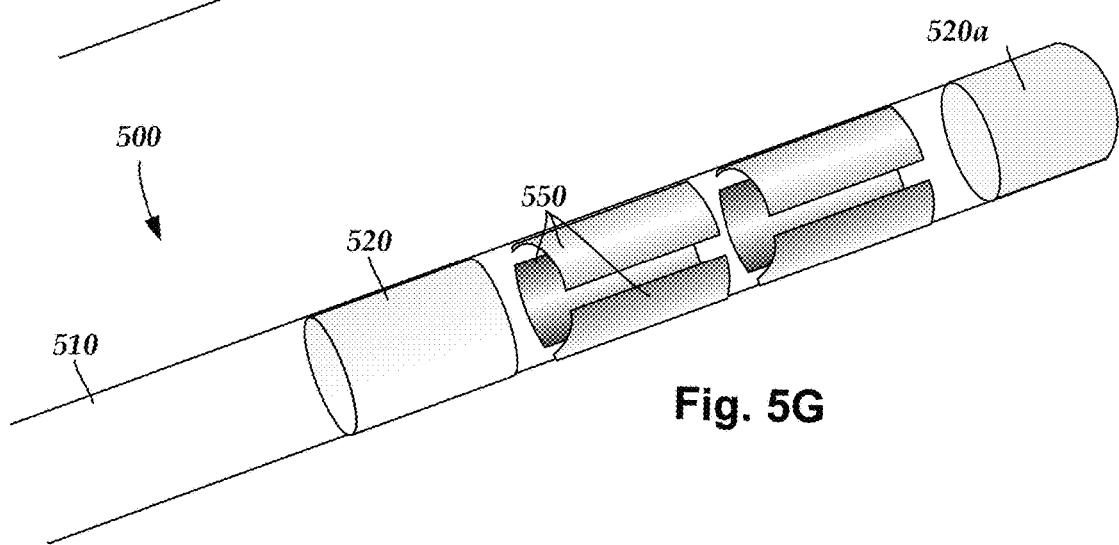
FIG. 5G is a schematic perspective view of a seventh embodiment of a distal end of a lead containing segmented electrodes, according to the invention.

Any combination of ring electrodes 520 and segmented electrodes 550 may be disposed on the lead 500. For example, the lead may include a first ring electrode 520, two sets of segmented electrodes; each set formed of four segmented electrodes 550, and a final ring electrode 520 at the end of the lead. This configuration may simply be referred to as a 1-4-4-1 configuration (FIGS. 5A and 5E—ring electrodes 520 and segmented electrode 550). It may be useful to refer to the electrodes with this shorthand notation. Thus, the embodiment of FIG. 5C may be referred to as a 1-1-4-4 configuration, while the embodiment of FIG. 5D may be referred to as a 4-4-1-1 configuration. The embodiments of FIGS. 5F, 5G, and 5H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 550 are disposed on the lead. The 1-3-3-1 electrode configuration of FIGS. 5F, 5G, and 5H has two sets of segmented electrodes, each set containing three electrodes disposed around the perimeter of the lead, flanked by two ring electrodes (FIGS. 5F and 5H) or a ring electrode and a tip electrode (FIG. 5G). In some embodiments, the lead includes 16 electrodes. Possible configurations for a 16-electrode lead include, but are not limited to 4-4-4-4; 6-8; 5-3-3-3-3-1 (and all rearrangements of this configuration); and 2-2-2-2-2-2-2-2. Any other suitable segmented electrode arrangements (with or without ring electrodes) can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference in their entirety.

In at least some embodiments, a lead with 16 electrodes also includes 16 terminals. Many conventional control modules and connectors are designed to accept a proximal end of a lead or lead extension with an array of eight terminals. To instead have 16 terminals could extend the length of the proximal end of the lead or lead extension and a consequent increase in the size of connector or control module.

Instead, in at least some embodiments it may be advantageous to design an elongate member (e.g., a lead, lead extension, splitter, adaptor, or the like) with segmented terminals forming a split proximal contact array. In at least some embodiments, the elongate member also includes segmented electrodes. Utilizing a split proximal contact array may reduce the physical size of the terminal array when compared to conventional terminal arrays with ring-shaped terminals. Consequently, the portion of the elongate member that is inserted into a connector to make electrical contact with the pulse generator can be reduced, as compared to conventional electrical stimulation systems. Alternately, the number of terminals that can be disposed along a proximal portion of an elongate member and that can be inserted into a conventionally sized connector may be increased from conventional electrical stimulation systems. Some examples of such arrangements are found in, for example, U.S. Provisional Patent Application Ser. No. 62/113,291, incorporated herein by reference in its entirety.

Although the embodiments described below are presented as leads, it will be understood that the arrangement of segmented terminals described below can also be applied to a lead extension or other elongate member having terminals or other contacts. In general, any elongate member can have first contacts (for example, electrode for a lead or conductive contacts for a lead extension) disposed along a distal portion of the elongate member and second segmented contacts (for example, segmented terminals) disposed along a proximal portion of the elongate member.

Figure 6A:
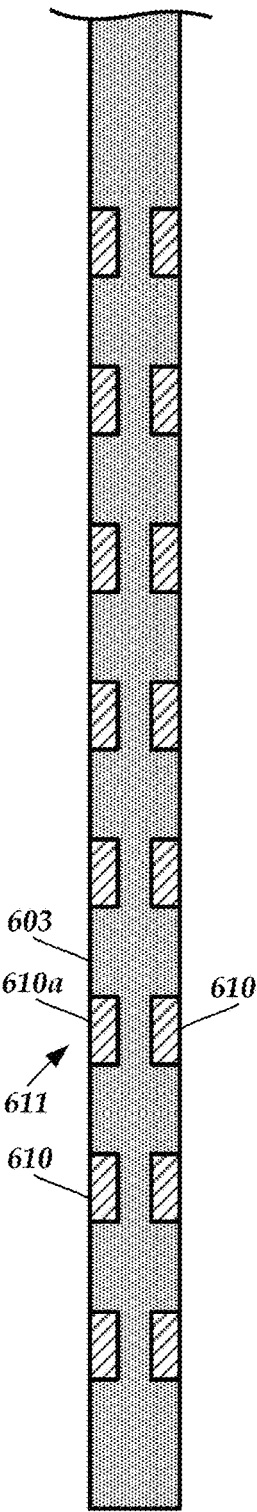
FIG. 6A is a schematic side view of one embodiment of a proximal end of a lead containing segmented terminals, according to the invention.

FIG. 6A illustrates one embodiment of a proximal portion of a lead 603 (or other elongate member) with a split proximal contact array of segmented terminals 610. Each of the segmented terminals extends around less than (for example, no more than 45%, 40%, 33%, 30%, or 25% of) the entire perimeter of the elongate member. In some embodiments, the terminal array is formed exclusively from segmented terminals. In other embodiments, the terminal array includes a combination of one or more ring-shaped terminals and one or more segmented terminals. The segmented terminals are not in electrical contact with one another.

In at least some embodiments, the terminal array includes at least one segmented terminal set disposed at a particular longitudinal position along the lead, such as segmented terminal set 611 which, in turn, includes multiple segmented terminals 610, such as segmented terminals 610a and 610b. In some embodiments, a set of segmented terminals can have two, three, four, or more segmented terminals disposed at the same position along the longitudinal axis of the elongate member, but circumferentially offset from each other. The terminal array can include any suitable number of segmented terminal sets 611 including, for example, one, two, three, four, five, six, seven, eight, nine, ten eleven, twelve, thirteen, fourteen, fifteen, sixteen, or more segmented-terminal sets. In FIG. 6A, eight segmented terminal sets 611 are shown disposed along the lead 603.

Other arrangements of segmented terminals can also be used including, but not limited to, helical arrangements, double helical arrangements, staggered arrangements, and the like. Any of the arrangements of segmented electrodes disclosed in the references cited above can be used with the segmented terminals.

In at least some embodiments, the elongate member includes a single proximal portion and multiple distal portions. One advantage of using segmented terminals is that this may increase the number of terminals disposed along a lead from conventional leads. The increased number of terminals may enable the lead to be designed with multiple distal portions, where a different electrode array is disposed along each of the distal portions, and where electrodes of each of the multiple electrode arrays are coupled to terminals disposed along a single proximal portion. Such a design may be useful, for example, in deep brain stimulation where bilateral or multilateral stimulation may be desirable.

Figure 6B:
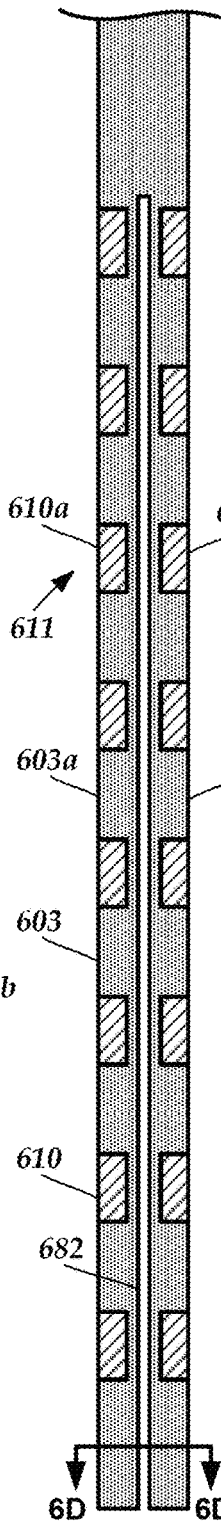
FIG. 6B is a schematic side view of a second embodiment of a proximal end of a lead containing segmented terminals, according to the invention.
Figure 6C:
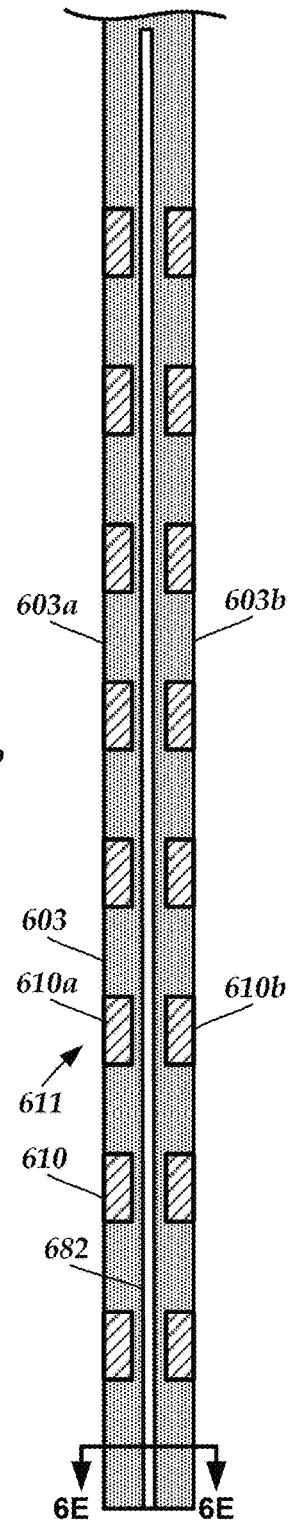
FIG. 6C is a schematic cross-sectional view of the lead of FIG. 6B, according to the invention.
Figure 6D:
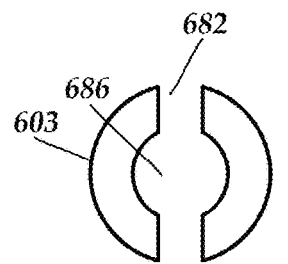
FIG. 6D is a schematic side view of a third embodiment of a proximal end of a lead containing segmented terminals, according to the invention.
Figure 6E:
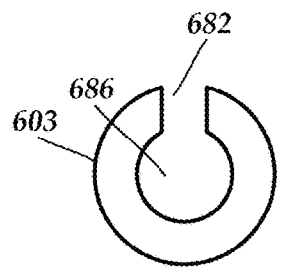
FIG. 6E is a schematic cross-sectional view of the lead of FIG. 6D, according to the invention.

In some embodiments, the lead 603 can have a slit 682 through the proximal portion of the lead, as illustrated in FIGS. 6B and 6D, or partially through the proximal end of the lead, as illustrated in FIGS. 6C and 6E, to separate the proximal portion of the lead into two parts 603a, 603b. The slit 682 separates (or partially separates) the terminals 610a, 610b in each set 611. In the embodiment of FIG. 6D, the slit 682 only extends partway into the lead 603 to the central lumen 686, as illustrated in FIG. 6E.

Figure 7A:
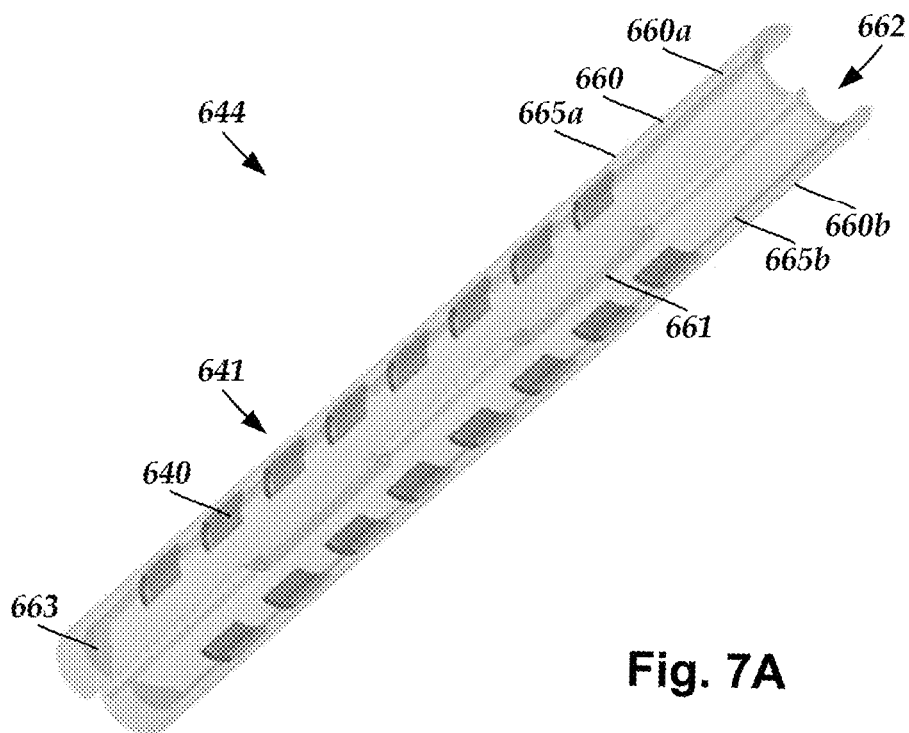
FIG. 7A is schematic perspective view of one embodiment of a connector for receiving a lead containing segmented terminals, according to the invention.
Figure 7B:
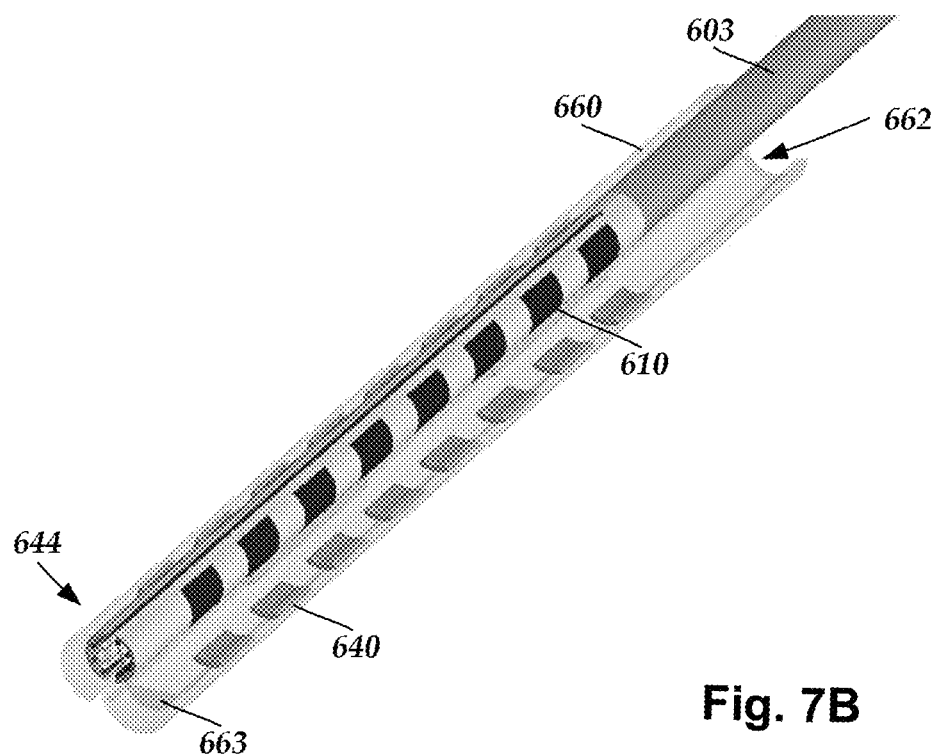
FIG. 7B is schematic perspective view of the connector of FIG. 7A receiving the lead of FIG. 6A, according to the invention.

Turning to FIGS. 7A and 7B, a proximal portion of an elongate member, such as the lead 603, is typically inserted into a connector 644 disposed on or along a lead extension, adaptor, splitter, or the like. The connector 644 includes segmented connector contacts 640 suitable for coupling with the segmented terminals. In at least some embodiments, a lead extension body (see, for example, lead extension body 325 of FIG. 3C) or other elongate member extends from the connector with conductors (not shown) the couple the segmented connector contacts 640 of the connector 640 to terminals on the proximal end of the lead extension.

The connector 644 includes an elongated connector housing 660 that defines a connector lumen 662 suitable for receiving a portion of an elongate member, such as the lead 603 (FIGS. 6A, 6B, and 6D); a lead extension (e.g., 324 in FIG. 3C); or the like. Although the illustrated connector lumen has a circular cross-section, it will be understood that lumens with other cross-sections (and leads with non-circular cross-sections) can also be used including, but not limited to, oval, square, rectangular, triangular, pentagonal, hexagonal, octagonal, cruciform, or any other suitable regular or irregular cross-sectional shape. In at least some embodiments, the connector 644 can have one or more end stops 663 that provide a physical barrier against insertion of the lead further into the connector.

The connector housing 660 has two portions 660a, 660b that are coupled together by one or more hinges 661 or other coupling elements to allow the connector housing 660 to be partially separated (as illustrated in FIGS. 7A and 7B) or otherwise opened for insertion of the lead 603 or other elongate member into the connector lumen 662. The connector can also be part of a header of a control module (see, for example, header 150 of control module 102 FIG. 1) where one portion of the connector housing 660 rotates or opens away from the header to allow insertion of the lead into the connector.

In at least some embodiments, the two portions 660a, 660b of the connector housing 660 can have a coupling arrangement along the edges 665a, 665b to facilitate coupling of the connector housing 660 in a closed position. Such coupling arrangements can be, for example, a tongue and groove arrangement along the edges 665a, 665b or magnets in the edges 665a, 665b that can be brought together to coupling the portions 660a, 660b of the connector housing 660 in the closed position. In some embodiments, the connector housing 660 may have an alignment protrusion (not shown) that can be received in the slit 682 (FIGS. 6B-6E) of the lead 603 to facilitate alignment of the lead within the connector housing.

Multiple connector contacts 640 are disposed in a spaced-apart relationship along the longitudinal length of the connector housing 660 such that the connector contacts are exposed to the connector lumen 662 (FIGS. 7A and 7B) and individually attached to an array of conductive members (for example, wires, pins, traces, terminals, or the like) that couple the connector contacts to other components. When, for example, the connector 644 is disposed on a lead extension (e.g., 324 in FIG. 3C), the conductive members (for example, wires or other conductors) may couple the connector contacts to lead extension terminals. When, for example, the connector 644 is disposed on a control module, the conductive members (for example, wires, traces, pins, or the like) may couple the connector contacts 640 to the electronic subassembly (110 in FIG. 1). In at least some embodiments, the conductive members 664 couple the connector contacts 640 to the electronic subassembly (110 in FIG. 1) via feedthrough pins extending through the sealed housing (114 in FIG. 1).

In at least some embodiments, the segmented connector contacts 640 can be formed in sets of two or more contacts at a same position along the longitudinal axis of the connector lumen 662. Each of the segmented connector contacts of a particular set extends around less than (for example, no more than 45%, 40%, 33%, 30%, 25%, 20%, 15%, or 10% of) the entire perimeter of the connector lumen. The segmented connector contacts of the set are not in electrical contact with one another and are circumferentially offset from one another along the connector lumen. In at least some embodiments, the connector contact array includes at least one connector contact set, such as connector contact set 641 which, in turn, includes multiple connector contacts 640, such as connector contacts 640a and 640b. In some embodiments, a set of connector contacts can have two, three, four, or more connector contacts disposed at the same position along the longitudinal axis of the connector lumen, but circumferentially offset from each other. Other arrangements of connector contacts can be used similar to those discussed above with respect to the segmented terminals.

In the embodiments of FIGS. 6A-6E, 7A, and 7B, one or more of the segmented terminals 610 of the lead 603 and one or more of the connector contacts 640 of the connector 644 are made of (or contain) magnetic material to attract each other and facilitate alignment of the segmented terminals with the connector contacts when the lead (or other elongate member) is inserted into the connector lumen of the connector. The magnetic segmented terminal(s) and magnetic connector contact(s) have opposite magnetic polarities so that the corresponding terminal/contact pairs are attracted to each other. In some embodiments, all of the segmented terminals 610 are magnetic and all of the connector contacts 640 are magnetic. In other embodiments, only some (for example, one, two, three, four, six, or more) of the segmented terminal 610 and some (for example, one, two, three, four, six, or more) of connector contact 640 are magnetic. As an example, one or both of the most proximal or most distal terminals of the lead and one or both of the most proximal or most distal connector contacts of the connector are magnetic. Other arrangements of magnetic and non-magnetic terminals/contacts can be used including, but not limited to, an alternating arrangement of magnetic/non-magnetic terminals/contacts or an arrangement where one terminal of each set of terminals and one contact of each set of contacts are magnetic. In yet another arrangement, each set of terminals can have a terminal of each polarity and each set of contacts can have a contact of each polarity. Any other suitable arrangement can be used. The magnetic terminals and contacts can be made of any suitable magnetic materials including, for example, neodymium or other rare earth magnets or ferromagnetic materials.

FIG. 8A illustrates another embodiment of a lead 603 that, instead of magnetic segmented terminals, includes magnetic elements 615 disposed between, or distal to or proximal to (or any combination thereof), the segmented terminals 610. The magnetic elements 615 can be magnetic spacers between, proximal to, or distal to the segmented terminals 610 or can be magnets disposed within the spacers. In at least some embodiments, the magnetic elements 615 are non-conductive and can be, for example, ceramic or composite magnets or magnetic material dispersed (or otherwise disposed) in a non-conductive matrix (for example, a polymeric matrix.) In at least some embodiments, the magnetic elements can be formed as at least one magnetic set which includes multiple magnetic elements, such as magnetic elements 615a and 615b.

FIG. 8B illustrates a corresponding connector 644 with magnetic connector elements 645 disposed between, distal to, or proximal to (or any combination thereof), the connector contacts 640. In at least some embodiments, the magnetic connector elements 645 are non-conductive and can be, for example, ceramic or composite magnets or magnetic material dispersed (or otherwise disposed) in a non-conductive matrix (for example, a polymeric matrix.) In at least some embodiments, the magnetic connector elements 645 can be formed as at least one magnetic set which includes multiple magnetic elements. The magnetic element(s) 615 of the lead 603 and magnetic connector element(s) 645 of the connector 640 should have opposite magnetic polarities so that they are attracted to each other.

In some embodiments, there is a magnetic element 615 between each adjacent pair of segmented terminals 610 and a magnetic connector element 645 between each adjacent pair of the connector contacts 640. In other embodiments, magnetic elements 615 are placed between only some (for example, one, two, three, four, six, or more) of the adjacent pairs of segmented terminals 610 and magnetic connector elements 645 are placed between only some (for example, one, two, three, four, six, or more) of the adjacent pairs of connector contacts 640. Other arrangements of magnetic elements 615 and magnetic connector elements 645 can be used including, but not limited to, magnetic elements 615 positioned distal to, or proximal to (or both), all of the segmented terminals 610 and magnetic connector elements 645 positioned distal to, or proximal to (or both), all of the connector contacts 640.

Figure 9:
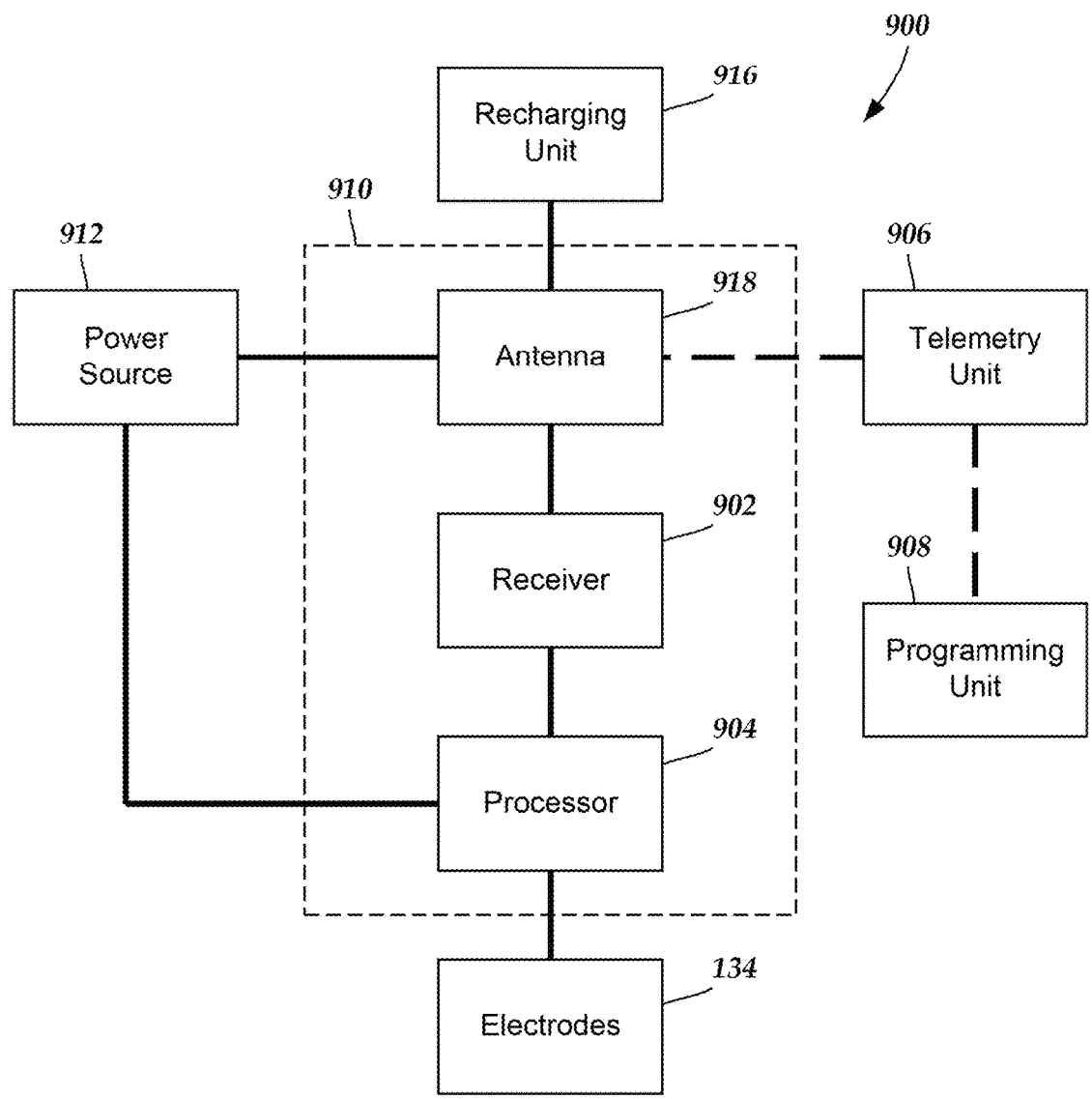
FIG. 9 is a schematic overview of one embodiment of components of an electrical stimulation system, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an implantable electrical stimulation device, the connector comprising:
   an elongated connector housing having a first end and an opposing second end, the connector housing comprising a first portion, a second portion, at least one coupling element attaching the first portion to the second portion, and a connector lumen defined by the first and second portions, wherein the first and second portions are configured and arranged to partially separate to receive a lead or lead extension into the connector lumen of the connector housing;
   a plurality of connector contacts disposed on the connector housing adjacent the connector lumen, wherein a first set of the connector contacts is disposed on the first portion of the connector housing and a second set of the connector contacts is disposed on the second portion of the connector housing; and
   a plurality of connector magnets comprising a plurality of first connector magnets disposed on the first portion of the connector housing and a plurality of second connector magnets disposed on the second portion of the connector housing and configured to align the lead or lead extension.

2. The connector of claim 1, wherein at least one of the connector contacts is a magnet.

3. The connector of claim 1, wherein the connector magnets are disposed within the connector housing.

4. The connector of claim 3, wherein at least one of the connector magnets is disposed between two of the connector contacts.

5. The connector of claim 1, wherein the first portion and the second portion of the connector housing have a tongue and groove arrangement along edges of the first and second portions to fasten the first and second portions in a closed position.

6. The connector of claim 1, further comprising at least one coupling magnet disposed on edges of each of the first and second portions to fasten the first and second portions in a closed position.

7. The connector of claim 1, wherein the at least one coupling element of the connector housing is at least one hinge.

8. A lead extension, comprising:
   the connector of claim 1;
   a lead extension body extending from the connector;
   a plurality of terminals disposed along a portion of the lead extension body opposite the connector; and
   a plurality of conductors extending along the lead extension body and the connector and electrically coupling the plurality of connector contacts to the plurality of terminals.

9. A control module, comprising:
   a header comprising the connector of claim 1;
   a housing coupled to a header; and
   an electronic subassembly disposed within the housing, wherein the electronic subassembly is electrically coupled to the connector contacts of the connector.

10. A system for electrical stimulation, comprising;
    the connector of claim 1; and
    an electrical stimulation lead coupleable to the connector, the electrical stimulation lead comprising
       an elongate lead body having a proximal end and a distal end opposite the proximal end,
       a plurality of electrodes disposed along the distal end of the lead body,
       a plurality of terminals disposed along the proximal end of the lead body, wherein each of the terminals extends around no more than 45% of a perimeter of the lead,
       a plurality of conductors extending within the lead body and electrically coupling the electrodes to the terminals, and
       a plurality of lead magnets disposed along the proximal end of the lead body and configured and arranged to couple to the connector magnets of the connector to align the proximal end of the lead within the connector lumen of the connector so that each of the terminals makes electrical contact with only one of the connector contacts of the connector.

11. The system of claim 10, wherein at least one of the connector contacts is a magnet and at least one of the terminals is a magnet.

12. The system of claim 10, wherein the connector magnets are disposed within the connector housing and the lead magnets are disposed along the lead body.

13. The system of claim 12, wherein at least one of the connector magnets is disposed between two of the connector contacts and at least one of the lead magnets is disposed between two of the terminals.

14. The system of claim 10, wherein the at least one coupling element of the connector housing is at least one hinge.

15. The system of claim 10, further comprising a lead extension, the lead extension comprising
   the connector;
   a lead extension body extending from the connector;
   a plurality of terminals disposed along a portion of the lead extension body opposite the connector; and
   a plurality of conductors extending along the lead extension body and the connector and electrically coupling the plurality of connector contacts to the plurality of terminals.

16. The system of claim 10, further comprising a control module, the control module comprising
   a header comprising the connector;
   a housing coupled to a header; and
   an electronic subassembly disposed within the housing, wherein the electronic subassembly is electrically coupled to the connector contacts of the connector.

17. The system of claim 10, wherein at least one of the lead magnets is disposed between two of the terminals.

18. A system for electrical stimulation, comprising;
   the connector of claim 1; and
   an electrical stimulation lead coupleable to the connector, the electrical stimulation lead comprising
      an elongate lead body having a proximal end and a distal end opposite the proximal end,
      a plurality of electrodes disposed along the distal end of the lead body,
      a plurality of terminals disposed along the proximal end of the lead body, wherein each of the terminals extends around no more than 45% of a perimeter of the lead, wherein at least one of the terminals is formed of a ferromagnetic material,
      a plurality of conductors extending within the lead body and electrically coupling the electrodes to the terminals.

19. The system of claim 18, wherein each of the connector magnets is a contact.

* * * * *